United States Patent [19]

Sakurai et al.

[11] Patent Number: 5,164,898
[45] Date of Patent: Nov. 17, 1992

[54] SYSTEM FOR DETERMINING HAZARDOUS SUBSTANCE EXPOSURE RATE FROM CONCENTRATION MEASUREMENT AND HEART RATE DATA

[75] Inventors: Haruhiko Sakurai, Sayama; Toshiaki Higashi, Kitakyushu; Toshihiko Satoh, Tokyo; Yutaka Tomita; Kohki Isago, both of Yokohama, all of Japan

[73] Assignee: Ricoh Company, Ltd., Tokyo, Japan

[21] Appl. No.: 835,036

[22] Filed: Feb. 10, 1992

Related U.S. Application Data

[63] Continuation of Ser. No. 361,552, Jun. 5, 1989, abandoned.

[30] Foreign Application Priority Data

Jun. 10, 1988 [JP] Japan .................... 63-143087

[51] Int. Cl.⁵ .................................. G06F 15/00
[52] U.S. Cl. ........................ 364/413.3; 364/413.03; 128/696; 73/31.02
[58] Field of Search .......... 364/413.3, 413.03, 413.05, 364/413.06; 128/671, 710, 696, 708; 346/45, 49; 73/31.02

[56] References Cited

U.S. PATENT DOCUMENTS

| | | | |
|---|---|---|---|
| 3,593,718 | 7/1971 | Krasner et al. | 128/419 P |
| 4,073,621 | 2/1978 | Bull et al. | 346/33 A X |
| 4,165,630 | 8/1979 | Felder et al. | 73/31.03 X |
| 4,221,223 | 9/1980 | Linden | 364/413.06 X |
| 4,519,398 | 5/1985 | Lisiecki et al. | 128/710 |
| 4,616,659 | 10/1986 | Prezas et al. | 364/413.06 X |
| 4,729,381 | 3/1988 | Harada et al. | 128/671 |
| 4,779,199 | 10/1988 | Yoneda et al. | 364/413.03 |
| 4,786,472 | 11/1988 | McConnell et al. | 73/31.02 X |
| 4,884,576 | 12/1989 | Alt | 128/419 PG |

OTHER PUBLICATIONS

Landry, T. D. et al. "Pulmonary physiology and inhalation dosimetry in rats: Development of a method and two examples", *Toxicology and Applied Pharmocology*, vol. 71, No. 1, Oct. 1983, 72-83.

Rossi, P. et al. "Respiration as a reliable physiological sensor for controlling cardiac pacing rate", *Br. Heart J. (England)*, vol. 51, No. 1, 1984, 7-14.

Primary Examiner—Roy N. Envall, Jr.
Assistant Examiner—Laura Brutman
Attorney, Agent, or Firm—Cooper & Dunham

[57] ABSTRACT

A device for measuring a rate exposed to deleterious materials comprises a heartbeat sensor for sensing heart rates, a deleterious material sensor for sening concentrations of deleterious materials in the air, a memory for storing the conversion values for converting the heart rates into corresponding respiration rates, and an operation unit. The operation unit counts a heart rate based a heartbeat signal received from the heartbeat sensor, calculates a respiration rate corresponding to the heart rate based on a conversion value read out from the memory, and calculates a rate exposed to deleterious material per unit time based on the calculated respiration rate and a signal respresenting a concentration of the deleterious material which signal is received from the deleterious material sensor.

10 Claims, 5 Drawing Sheets

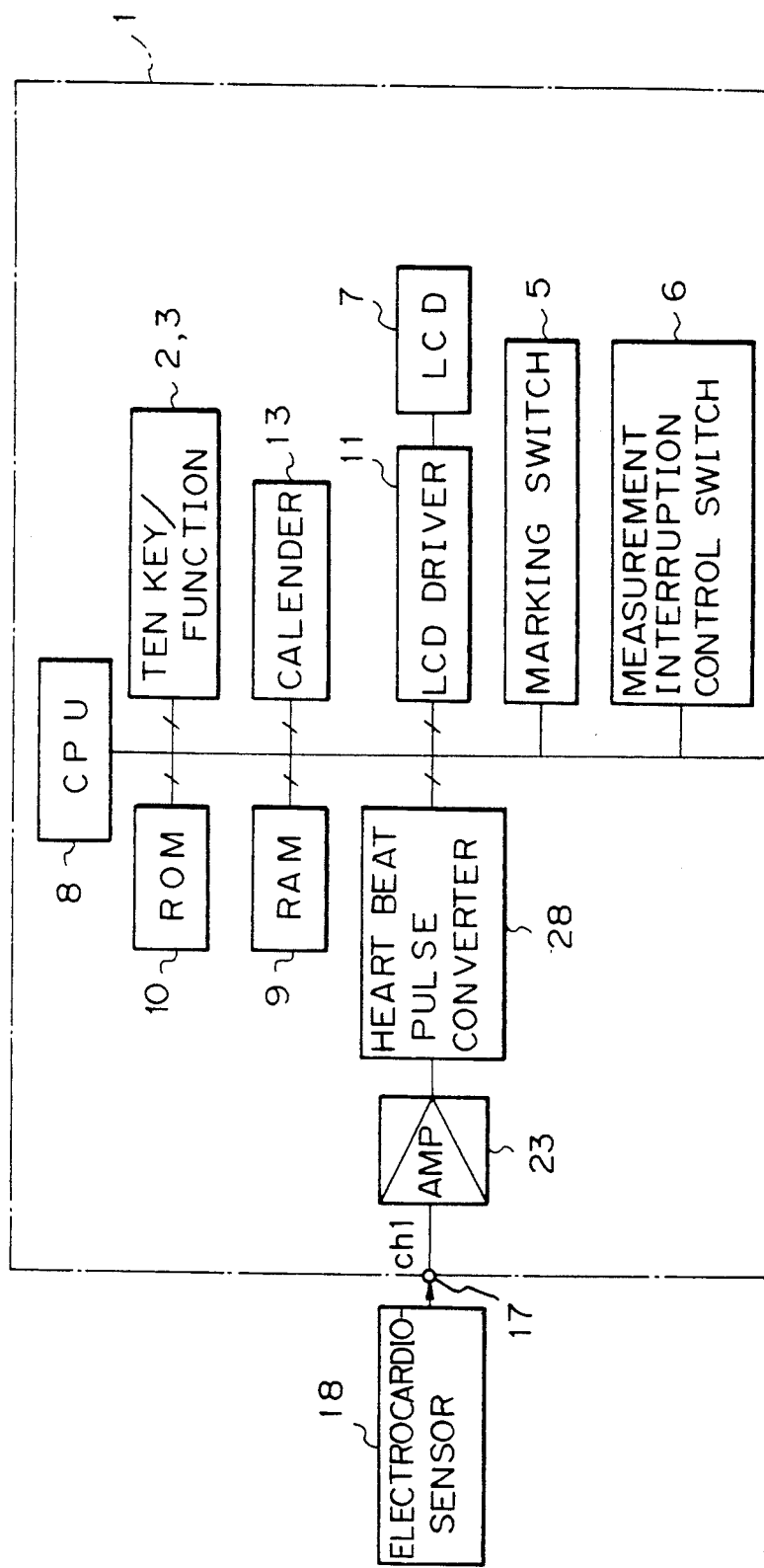

2

SYSTEM FOR DETERMINING HAZARDOUS SUBSTANCE EXPOSURE RATE FROM CONCENTRATION MEASUREMENT AND HEART RATE DATA

This is a continuation of application Ser. No. 361,552 filed Jun. 5, 1989, now abandoned.

BACKGROUND OF THE INVENTION

The present invention relates to a device for measuring the rate exposed to deleterious materials corresponding to an amount of physical labor in working environments in which physical labor in the field of the social medical science is performed.

Recently, the materials in the air detrimental to health, such as particle dust, organic solvent, and fiber dust of asbestos, have become an object of public concern. Particularly in working environments of high concentration of such deleterious materials, laborers work while being exposed to these deleterious materials. The steady improvement of such working environments has been made by measuring the rate of exposed to the deleterious materials, which rate corresponds to an amount of his labor. Socially this is of great importance.

The physiology clearly describes that the larger the physical load is, the higher a heart rate of a man is, and this is due to the fact that an increase of physical load increases his respiration rate. To make the improvement, therefore, it is required to set up standards of the tolerable concentrations of the deleterious materials in the working environments, and to constantly supervise the concentrations of the materials. In this case, the actual tolerable concentrations of the materials must be set to be somewhat lower than those specified by the standards with respect to environment where labor with large physical load is performed. This is true socially and economically.

A conventional methodology to measure the rate exposed to such harmful materials collects two types of data, living organism data and ambient condition data by individual measuring instruments. The living organism data contain heart rate, respiration rate, amounts of physical labor, and the like. The ambient condition data contain temperature, humidity, and concentrations of harmful materials in the atmosphere. The collected data are statistically analyzed for determining the rate exposed to the deleterious materials.

The above approach, however, necessitates the increased size of measuring instruments, and consequently limited applications of the resultant instruments, viz., limits the use of the instruments only in indoor work. Advantage of the approach is high measuring precision. Disadvantages reside in that it is very difficult to synchronously follow instantaneously changing working environments, and that mistake in data processing is inevitable, and the measured data on the rate exposed to the deleterious materials is unsatisfactory in reliability. Further, the particle dust measuring instruments commercially available function only to measure the amount of particle dust, and fail to play a helpful role in the improvement of the working environment.

Particularly in working environments of broad space where a relatively heavy body work is done, for example, in outdoor work, the conventional measuring instruments are almost incapable of measuring the deleterious materials qualitatively or quantitatively.

Further, the conventional measuring instruments is lack of a variety of other important functions to be required in the measurement. For example, in the measurement of the deleterious materials, it should be avoided that use of the instruments disturbs or interrupts laborer's work. Nevertheless, when a respiration rate of a laborer is measured by the conventional instrument, he must stop his work for the measurement.

SUMMARY OF THE INVENTION

Accordingly, an object of the present invention is to provide means to solve the above problems of the conventional measuring instruments.

To achieve the above object, there is provided a device for measuring a rate exposed to deleterious materials, comprising a heartbeat sensor for sensing heart rates, a deleterious material sensor for sensing concentrations of deleterious materials in the air, memory means for storing the conversion values for converting the heart rates into corresponding respiration rates, and an operation unit for counting a heart rate based on a heartbeat signal received from the heartbeat sensor, for calculating a respiration rate corresponding to the heart rate based on a conversion value read out from the memory means and for calculating a rate exposed to deleterious material per unit time based on the calculated respiration rate and a signal representing a concentration of the deleterious material, which signal is received from the deleterious material sensor.

The measuring device according to the present invention further includes an additional memory for storing the results of measurements, the additional memory being removably set to the main frame of the measuring device.

To measure a rate exposed to deleterious material, it is only needed to know the amount of the deleterious material in the air, and a respiration rate of a man under measurement as well. Nevertheless, the conventional measurement holds back the action of a laborer as an object under measurement when his respiration rate is measured. The inventor(s) of the present patent application empirically confirmed that there is a close correlation between a heart rate and a respiration rate of a man. Particularly in working environments where a relatively heavy physical work is done, for example, in outdoor work, our experiments showed that there is a linear relationship between the heart rate and the respiration rate. In the present invention, on the basis of this fact, the conversion values for converting heart rates into corresponding respiration rates are prestored in the memory. In place of measuring respiration rates, the waveforms of heartbeat signals are measured by means of the heartbeat sensor which will little holds back the action of the laborer. If necessary, the heartbeat signal is converted into a heartbeat pulse signal by a heartbeat pulse converter. The operation unit counts a heart rate using the heartbeat pulse signal. The operation unit works out a respiration rate of the laborer using the related conversion value. Meanwhile, the concentrations of deleterious materials in the atmosphere are sensed by a sensor exclusively used for sensing such materials. If necessary, a sensing signal is digitized into a digital signal reflecting a variation of the amplitude of the sensing signal, by an analog-to-digital (D/A) converter. The operation unit qualitatively and quantitatively processes both the data obtained from the heartbeat sensor and the deleterious material sensor, to qualitatively and quantitatively the rates exposed to the deleterious materials per unit time. The data thus obtained are stored into an external memory. The result of the rate exposed to the deleterious materials is stored in an external memory means.

As described above, a heart rate derived from a measured heartbeat signal waveform is converted into a respiration rate on the basis of the correlation between the heartbeat rate and the respiration rate. The respiration rate thus obtained and a concentration of each deleterious material, which concentration is obtained from the deleterious material sensor, are properly processed to work out a rate exposed to the deleterious material. This is realized with mere provision of a heartbeat sensor which little holds back the action of a laborer upon measuring the heartbeat, in addition to the sensor for sensing deleterious materials. In the case of using the measuring device according to the present invention, the rate exposed to the deleterious materials can be measured smoothly and in real time manner, without any interruption and alteration of the work of laborers. Further, if an external memory is used, the results of the measurements is stored into the external memory, and may be applied to another analyzer for statistically analyzing the data. The data thus analyzed data may be used for determine additional standards of the tolerable amounts of dangerous materials in working environments.

Further objects, features and advantages of the present invention will be apparent from the following description taken in connection with the accompanying drawings.

DETAILED DESCRIPTION OF THE PREFERRED EMBODIMENTS

Figure 1B:
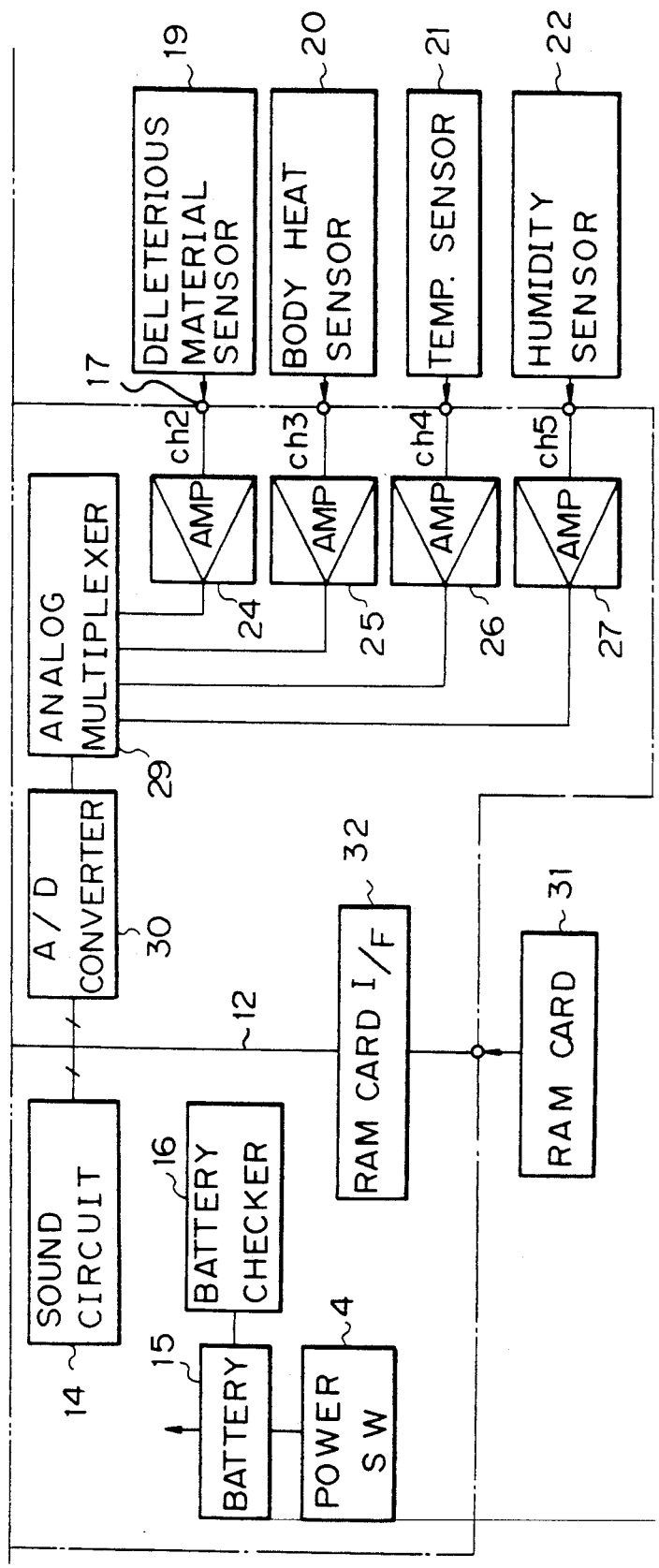
FIG. 1 constituted by FIGS. 1A and 1B, is a block diagram showing a configuration of a device for measuring the rate exposed to the deleterious materials according to a preferred embodiment of the present invention.
Figure 2A:
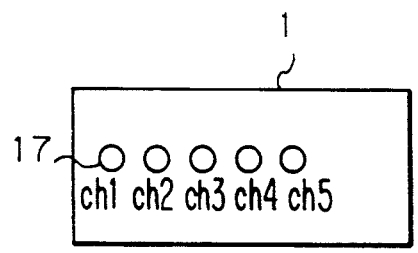
FIG. 2a shows a plan view of a main frame of the measuring device of FIG. 1.
Figure 2B:
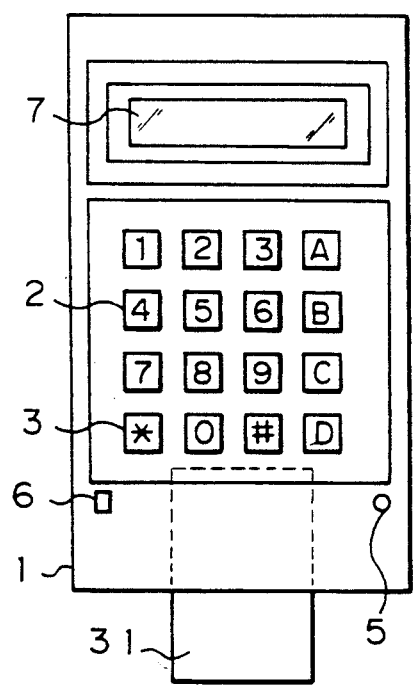
FIG. 2b shows a front view of a main frame.
Figure 2C:
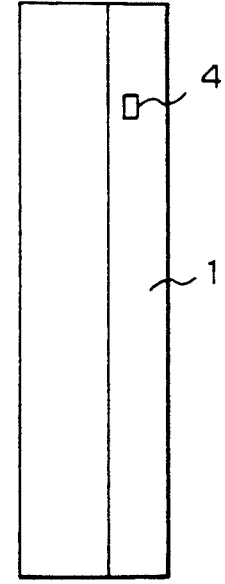
FIG. 2c shows a side view of the main frame.

FIG. 1 is a block diagram showing a configuration of a measuring device for measuring the rate exposed to the deleterious materials according to an embodiment of the present invention. FIG. 2 shows an appearance of the measuring device. As shown, a main frame 1 of the measuring device of the portable type, like that of an electronic calculator, is provided with ten keys 2 including 0 to 9 and function keys 3 marked with A, B, C, D, *, #, and the like. These keys 2 and 3, which are installed on one of the major surfaces of the main frame 1, serve as input means. In measuring the rate exposed to the deleterious materials, these keys 2 and 3 are used by a user for presetting measuring conditions before measurement, specifically for inputting the items for measurement such as ID code of a laborer under measurement, date, time, and measuring intervals of each channel. A power switch 4, marking switch 5, and control switch 6 for interrupting a measurement are additionally provided. The switches 5 and 6, which may be turned on and off, are operated by a laborer under measurement in some specific situations, for example, when an accidental phenomenon such as abnormal motions occur in his body or when he must temporarily stop his measurements, for example, for having a meal.

A liquid crystal display (LCD) 7 as display means is located above the keys 2 and 3. The LCD 7, that is capable of displaying 16 characters×2 lines, is used mainly when a user presets the items of measuring conditions or when measuring error occurs or the measuring device improperly operates.

Electrically, the main frame 1 of the measuring device contains a CPU 8 as a microprocessor, RAM 9, ROM 10, and the like. The CPU 8, which is made up of an 8-bit microprocessor, time-sequentially executes the measurement control of analog signals inputted through channels ch1 to ch5, and necessary data processing in accordance with a program stored in the ROM 10. The RAM 9 is used for temporarily storing parameters necessary for the measurement control such as the measuring conditions. The RAM 9, ROM 10, keys 2 and 3, switches 5 and 6, and LCD driver 11 for driving the LCD 7 are connected to the CPU 8 by means of the data bus 12. A calender 13 is also coupled with the data bus 12. The calender 13 is constructed with an IC with a preset terminal, which is used for an ordinary digital wrist watch. The calender 13 is used for checking measuring intervals during a measurement, and measuring time. A sound circuit 14 has such a circuit arrangement as to generate an ordinary electronic sound in response to control signals. When the measuring device improperly operates, the items of the measuring conditions have been preset, a battery is used up, and the like, the sound circuit 14 operates to generate an electronic sound and informs a user or a laborer of it. The present measuring device is portable and operable by a battery is contained. A battery checker 16 also contained constantly checks a power voltage of the battery when the measurement progresses.

Five terminals 17 marked with ch1 to ch5 to be coupled with sensors respectively for different measured items are mounted on the top end face of the main frame 1 of the present measuring device. Of these terminals 17, the terminal ch1 is to be coupled with an electrocardiosensor 18 as one example of the heartbeat sensors; the terminal ch2, with a deleterious material sensor 19; the terminal ch3, with a body heat sensor 20; the terminal ch4, with an ambient temperature sensor 21; the terminal ch5, with an ambient humidity sensor 22, when the coupling is required. To obtain a cardiogram, the electrocardiosensor 18 of the three-pole induction type is fixed to the body of a laborer under measurement by an adhesive-backed tape, for example. The deleterious material sensor 19 senses concentrations of deleterious materials, such as particle dust and organic solvent, in the air by an optical process or in the form of a variation of resistance of a vapor deposited film when it absorbs organic materials. The sensor section (sensing part) of the sensor is located near the measuring device when it is attached to the body of a laborer. If necessary, it may be mounted integrally to a suitable portion of the outer circumferential edges of the main frame 1. The body heat sensor 20 is made of solid-state electronic material and may be a thermistor or an IC temperature sensor. The sensor 20, like the electrocardiosensor 18, is fixed to a portion of the laborer's body suitable for sensing body heat, such as a part of the abdomen of the laborer. The ambient temperature sensor 21 is made of the material similar to that of the body heat sensor 20, but in a temperature resolution, the sensor 21 is more coarse than the sensor 20. The humidity sensor 22 in this instance is of the type which senses ambient humidity in terms of a variation of resistance of the used material when it absorbs water vapor in the atmosphere. These sensors 21 and 22 may be mounted to the main frame 1 per se as in the case of the deleterious material sensor 19. Alternatively, these may be located near the main frame, and connected to the related terminals of it by lead wires. If necessary, the coupling of the sensors and the related terminals 17 may be made wirelessly.

The sensing signals delivered from these sensors 18 to 22 are analog signals and their levels are different from one another. For this reason, these sensing signals are amplified up to a reference level, e.g., a TTL level, by means of the amplifiers 23 to 27, and then are led to the data bus 12. To be more specific, the terminal 17 denoted as ch1, exclusively used for the electrocardiosensor 18, transfers a sensing signal from the electrocardiosensor 18 to the amplifiers 23. The amplified sensing signal goes to the CPU 8, by way of a heartbeat pulse converter 28 as a heartbeat pulse converting means and of the data bus 12. The sensing signals from the remaining sensors 19 to 22 are amplified by the amplifiers 24 to 27, and are led to the CPU 8 by the data bus 12, by way of an analog multiplexer 29 and an A/D converter 30 as an analog-to-digital converting means. The arrangement of the deleterious material sensor 19 is not of the fixed terminal type, but if an object to be measured is changed to another, it is compatible with the new object in measurement operation. At the time of setting measuring conditions, the sensor is conditioned in connection with an object to be measured. The data concerning the conditioning is previously stored in the ROM 10, for each object. Such an arrangement enables the measuring device to cope with alteration of the specifications of the measuring device, without any modification of the hardware. The electrocardiosensor 18 and the deleterious material sensor 19 are essential to the present embodiment. The remaining sensors 20 to 22 are for collecting the reference data showing the details of working environments and physical load of the laborers, and in this sense these are optional. If necessary, other sensors for collecting living organism data such as blood pressure, work done, and electricity as is generated in association with the activity of muscle, may additionally be used, with an increased number of channels.

A RAM card 31 as an external or additional memory means is removably set to the main frame 1. When set to the main frame 1, it is coupled with the CPU 8 through a RAM card interface 32. The RAM 31 is a data storing medium for continuously storing the data that are inputted through channels ch1 through ch5. The RAM 31, containing a back-up battery, keeps for a long time the abilities to retain the data and to allow data transfer to and from the RAM per se. If an electrically erasable read only memory (E²ROM) is used for the RAM 31, the above abilities can be permanently secured without the battery.

With the above mentioned arrangement, use of the electrocardiosensor 18 is one of the major features of this embodiment. The chief aim of the electrocardiosensor 18 is to measure a heart rate of a laborer, and not to recognize patterns of the cardiogram. The inventors found in their experiments that there is a close correlation between a heart rate and a respiration rate of a man. This will be described in details below.

Figure 3:
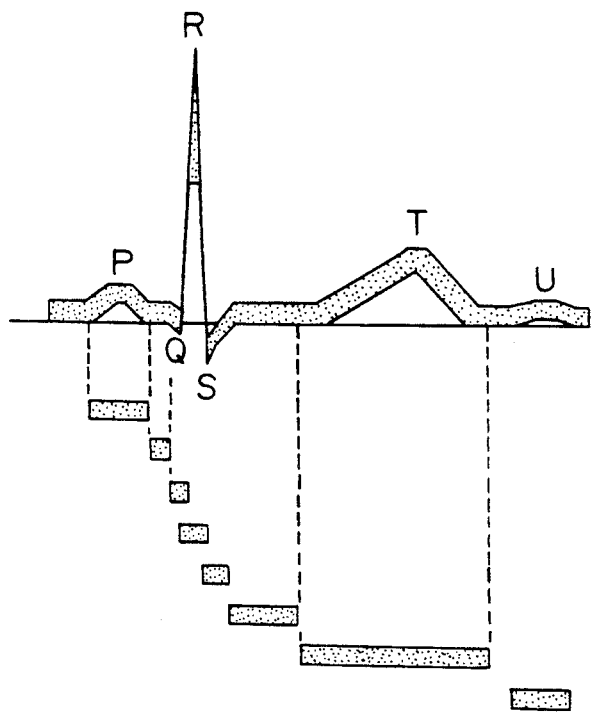
FIG. 3 shows a typical cardiogram.

FIG. 3 shows a typical electrocardiogram which is used for clinically diagnosing a patient suffering from a heart disease. The present embodiment does not treat the patterns of the electrocardiogram, but utilizes the R wave in the electrocardiogram for calculating a heart rate, and uses the electrocardiosensor 18 for sensing a heart rate with a high precision, which electrocardiosensor is the same as the cardiogram. To make the above clear, the electrocardiogram will be described in brief. Generally, an electrocardiogram for a man of health has a specific pattern representing a normal heart action, as shown in FIG. 3. As shown, the pattern of the electrocardiogram consists of a succession of waves P, Q, R, S, T and U. When a man suffers from a heart disease and his heart action is irregular, the pattern is deformed. The type of disease specifically deforms the pattern of the electrocardiogram. The deformed patterns are classified into categories called Minnesota codes, which specify respectively the names of diseases.

A heart rate can be obtained by merely measuring the number of pulses representing heartbeats per time. The R wave is utilized for measuring the number of heartbeat pulses. The reason why the R wave is utilized resides in that the R wave is very steep in inclination and large in amplitude, and therefore its detection is easy and it can be converted into the heartbeat pulse with a high precision.

Figure 4A:
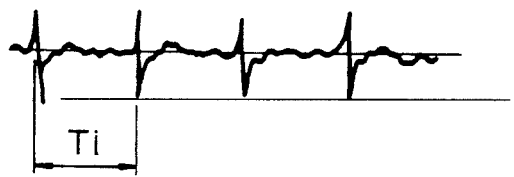
FIG. 4, (a) and (b), show two types of cardiograms, one measured before work is done and the other when work progresses.
Figure 4B:
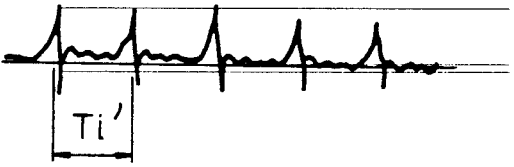

The larger a load for a man is or the longer a duration of the load existence is, the heart rate is larger. Cardiograms of a living body were traced in two different conditions, before he works and when he engages in light work. The resultant cardiograms are as shown in FIGS. 4(a) and 4(b). Assuming that an interval between two adjacent R waves is defined as a beat period, and the beat period before work is done is Ti, and the beat period when the work progresses is Ti', we have the following relationship between the two beat periods, $$Ti > Ti'.$$

The above relation teaches that when a physical load is applied, the heart rate increases.

Figure 5:
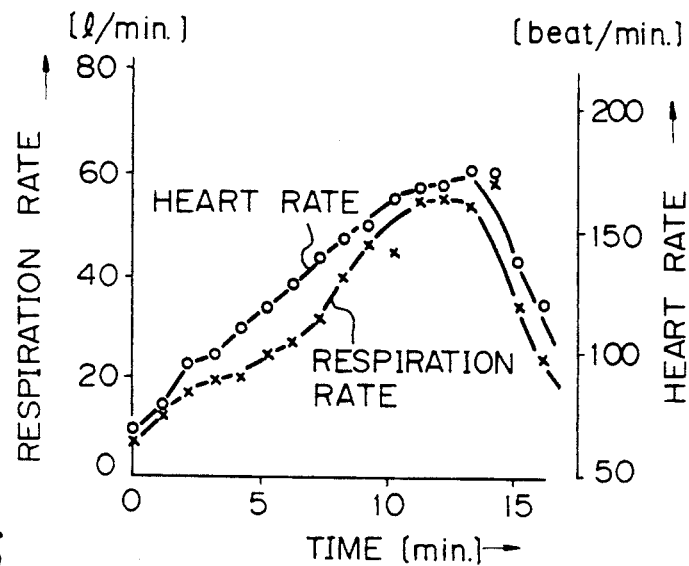
FIG. 5 shows a graphical representation of relationships between a respiration rate and a heartbeat rate vs. time.
Figure 6:
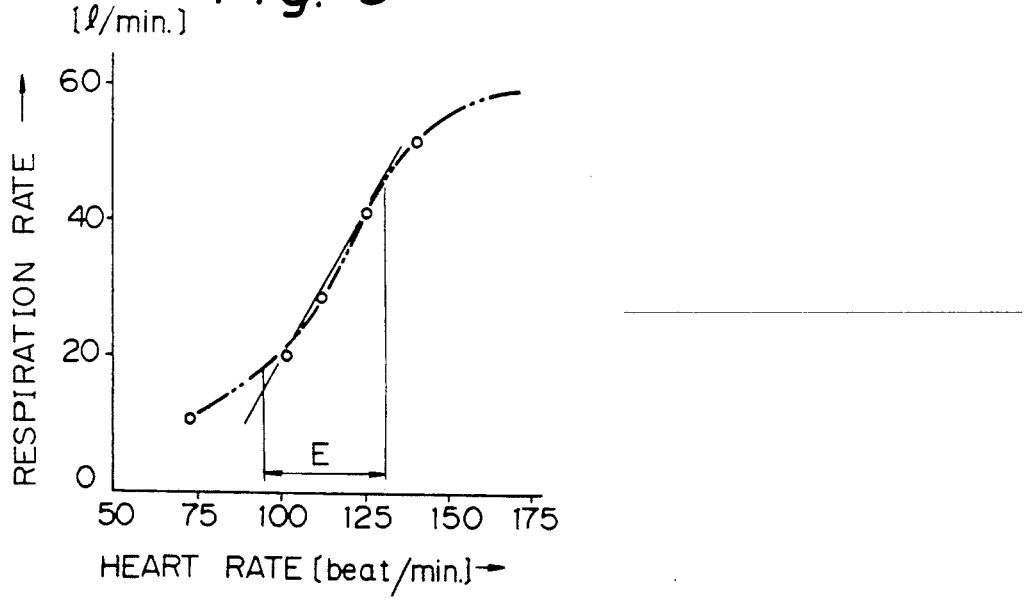
FIG. 6 shows a graphical representation of a relationship between a respiration rate vs. a heart rate.
Figure 7A:
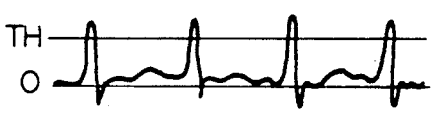
FIG. 7, (a) and (b), show waveforms useful in explaining the operation of a heartbeat pulse converter.
Figure 7B:

There were measured a heart rate and a respiration rate of healthy man who treaded on a treadmill which is usually used for health promotion. The results of the measurement are illustrated in FIG. 5. A relationship between the heart rate vs. respiration rate may be depicted as shown in FIG. 6, on the basis of the data plotted in FIG. 5. In FIG. 6, 75 on the heart rate axis indicates a heart rate of a healthy man (corresponding to the cardiogram of FIG. 4(a)). Character E indicates a range of a variation of the heart rate when the man works. The graph of FIG. 6 indicates a nice correlation between the heart rate and respiration rate. In such a working environment that a relatively strong physical load is applied as in outdoor work, the respiration rate approximately linearly increases with respect to the heart rate as typically represented by the range E. This fact implies that, to measure the rate exposed to deleterious materials, there is no need for performing the conventional respiration rate measurement for which a man under measurement is held back in actions, and it is only needed that a heart rate is measured and converted into a corresponding respiration rate. On the basis of this fact, in the present invention, the electrocardiosensor 18 is used for measuring a heart action of a laborer, for example, and obtaining his cardiogram. For the measurement, the electrocardiosensor 18 little holds back the action of the laborer. The results of the measurement are converted into pulses of a heart rate. The conversion is done by the heart rate pulse converter 28. The CPU 8 counts the number of pulses within a fixed period of time, to produce a heart rate. The heart rate pulse converter 28 consists of a comparing circuit arrangement using an operational amplifier. In the circuit arrangement, a waveform of the cardiogram derived from the electrocardiosensor 18 is compared with a preset threshold level TH (see FIG. 7 (a)). A pulse train obtained is applied to the CPU 8 (see FIG. 7(b)).

An analog signal, which is generated by the deleterious material sensor 19 and appears at the channel ch2, varies in amplitude in accordance with measured values, or concentrations of each deleterious material. The analog signal is applied through the analog multiplexer 29 to the A/D converter 30 where it is digitized. The digital signal obtained is led to the CPU 8 by the data bus 12. The other analog signals that are generated by the remaining sensors 20, 21 and 22 and appear at the channels ch3, ch4 and ch5, also vary in amplitude in accordance with the measured values, respectively. Accordingly, each of these signals is also processed in a similar way. Specifically, it is applied through the analog multiplexer 29 to the A/D converter 30 where it is digitized. The digitized signal is led to the CPU 8 by the data bus 12. The analog multiplexer 29 selectively receives one of the signals at the channels ch2 to ch5, in accordance with a control signal from the CPU 8.

Description to follow deals with an algorithm to work out the rate exposed to deleterious materials, which is used in the measuring device thus arranged. As recalled, a respiration rate b(t) is a function of a heart rate e(t), and may be expressed by $$b(t) = F\{e(t)\}. \quad (1)$$

where
t: time (minute) for measurement
e(t): heart rate (beats/min.)
b(t): respiration rate (1/min.).
An amount of deleterious material m(t) [μg/min.] contained in an inhaled air per unit time is given by $$\begin{aligned} m(t) &= p(t) \times b(t) \\ &= p(t) \times F\{e(t)\}, \end{aligned} \quad (2)$$

where
p(t): amount of deleterious material (μg/l) in the atmosphere.
The above relation (2) indicates that the amount of a deleterious material, viz., an amount of deleterious material m(t) contained in the air enhaled into the respiratory organ of a man under measurement per unit time, can be obtained by measuring a heart rate e(t) of the man to be measured and the amount of a deleterious material p(t) in air.

From the relation (2), a total rate exposed to deleterious material M as obtained when a laborer physically works from time t1 to time t2, can be written as $$M = \int_{t_1}^{t_2} m(t)dt = \int_{t_1}^{t_2} p(t) \times F[e(t)] \quad (3)$$

Assuming that actually, a sampling is made and hence with "n" of the number of samplings during a period from time t1 to time t2, the relation (3) can be rewritten into $$M = \sum_{i=1}^{n} pi \times F(e_i), \quad (4)$$

where pi indicates an amount of a deleterious material contained in the air at the time of the i-th sampling, and $e_i$ a heart rate at the time of the i-th sampling.

The conversion values for converting heart rates into corresponding respiration rates, as are defined by the relation (1) are previously stored in the ROM 10. The CPU 8 reads out a desired conversion value from the ROM 10, and converts a heart rate coming through the electrocardiosensor 18 and the heart rate pulse converter 28 into a corresponding respiration rate. Then, the CPU 8 processes the converted respiration rate and the digital data representing the amount of deleterious material that comes from the sensor 19 by using the algorithm as defined by the relation (2) or (4), and provides a rate exposed to deleterious material per unit time or a total rate exposed to deleterious material for a work time.

For the relations (2) and (4), the measuring interval may be variable. In this case, a cardiogram and a concentration of deleterious material are consecutively measured within a measuring interval that may be preset. In the case of a deleterious material whose concentration rapidly changes, such as an organic solvent, the measuring interval in the relation (2) and (4) is set to be short.

The b(t) in the relation (1) also indicates an amount of inhaled air of a man under measurement. An amount of a deleterious material accumulated in his body may be determined by measuring and using a concentration of a deleterious material contained in the inhaled air. Accordingly, if the relationship between them is previously determined, the amount of the accumulated deleterious material may be determined. In this case, a table storing the values for converting the concentrations of the deleterious material into the amounts of the accumulated material is convenient. Thus, the accumulated deleterious material as well as the inhaled deleterious material can be obtained.

In the present embodiment, the rate exposed to deleterious materials per unit time and the total rate exposed to deleterious material for a given work time are measured and obtained in real time, together with date and ambient temperature, are stored into the RAM card 31. Use of the RAM card 31 enhances the management of the data of individual men. Further, when the RAM card 31 is applied to an analyzer such as a microcomputer commercially available, desired standards of the working environments can statistically be determined. In such a case, if required, the data of only the concentration of deleterious material p(t) and the heart rate e(t) are stored in the RAM 31. The operation of the relation (2) and (4) for obtaining the rates exposed to deleterious materials may be performed by the analyzer.

In the above-mentioned embodiment, the electrocardiosensor 18 is used for the sensor sensing heartbeats. The sensor 18 may be substituted by any type of sensor, if it can sense cardiac cycles, such as a sensor for sensing the sounds of the heart and a sensor for sensing pulse rates.

The measuring device according to the present embodiment may be packaged into a small housing. Particularly, if the circuit arrangement shown in FIG. 1 is fabricated into a custom IC, the measuring device may be housed into a small frame comparable in size with recent small calculator, whereby an excellent portability is secured. With the excellent portability, in both indoor and outdoor working environments where physical work is done, the measuring device can continuously and qualitatively measure the rate exposed to deleterious materials corresponding to time varying physical loads and concentrations of such materials with little restricting laborers in action and without interrupting and altering their work. Therefore, the measuring device according to the present invention will greatly contribute to the improvements of working environments.

It is evident that the measuring device according to the present invention is also applicable for the monitor of living organism information for health promotion, particularly for handy and portable monitors for daily health care.

Many widely different embodiments of the present invention may be constructed without departing from the spirit and scope of the present invention. It should be understood that the present invention is not limited to the specific embodiment described in the specification, except as defined in the appended claims.

What is claimed is:

1. A portable device for measuring the rate of exposure of an individual to deleterious materials, comprising:
    a heartbeat sensor for sensing an individual's heart rate and for generating a heartbeat signal;
    heartbeat pulse converting means for converting said heartbeat signal into a heartbeat pulse signal;
    a deleterious material sensor for sensing a concentration of deleterious material in the air and for generating a signal p(t) representing the sensed concentration, where "t" is a time of sensing of said concentration;
    memory means for storing conversion values for converting a heart rate e(t) into a corresponding respiration rate b(t); and
    an operation unit for calculating a heart rate e(t) based on said heartbeat pulse signal from said heartbeat pulse converting means, for calculating a respiration rate b(t) corresponding to said heart rate e(t) based on a conversion value read out from said memory means, and for calculating a rate m(t) of exposure to deleterious material per unit time based on said calculated respiration rate b(t) and said concentration of deleterious material p(t) from said deleterious material sensor, said rate m(t) being given by $$m(t) = p(t)b(t)$$
$$= p(t)fn\{e(t)\}.$$

2. A portable device for measuring the rate of exposure to deleterious materials according to claim 1, further comprising digital conversion means for converting a signal m(t) representing the concentration of deleterious material from said deleterious material sensor into a digital signal corresponding to an amplitude of said signal m(t) representing the concentration of the deleterious material.

3. A portable device for measuring the rate of exposure to deleterious materials according to claim 1, further comprising removable additional memory means for storing the rate m(t) of exposure to deleterious materials calculated by said operation unit.

4. A portable device for measuring the rate of exposure to deleterious materials according to claim 3, in which said removable additional memory means is a card-type external memory means.

5. A portable device for measuring the rate of exposure to deleterious materials according to claim 1, further comprising means for setting conditions for measuring the rate of exposure to deleterious materials.

6. A portable device for measuring the rate of exposure to deleterious materials according to claim 5, in which said setting means comprises keys for inputting said measuring conditions.

7. A portable device for measuring the rate of exposure to deleterious materials according to claim 1, further comprising display means for displaying the rate m(t) of exposure to deleterious material calculated by said operation unit.

8. A portable device for measuring the rate of exposure to deleterious materials according to claim 1, in which said memory means is a ROM.

9. A portable device for measuring the rate of exposure to deleterious materials according to claim 1, in which said operation unit is a microprocessor.

10. A portable device for measuring the rate of exposure to deleterious materials according to claim 1, further comprising coupling means for supplying said heartbeat signal to said heartbeat pulse converting means in a wireless manner.

* * * * *